US006607896B1

(12) United States Patent
Millar et al.

(10) Patent No.: US 6,607,896 B1
(45) Date of Patent: Aug. 19, 2003

(54) DIAGNOSTIC TEST

(75) Inventors: Michael Millar, Bristol (GB); Tony Corfield, Bristol (GB)

(73) Assignee: University of Bristol, Bristol (GB)

( * ) Notice: Subject to any disclaimer, the term of this patent is extended or adjusted under 35 U.S.C. 154(b) by 0 days.

(21) Appl. No.: 09/936,600

(22) PCT Filed: Mar. 17, 2000

(86) PCT No.: PCT/GB00/01005

§ 371 (c)(1),
(2), (4) Date: Jan. 18, 2002

(87) PCT Pub. No.: WO00/55354

PCT Pub. Date: Sep. 21, 2000

(30) Foreign Application Priority Data

Mar. 17, 1999 (GB) .............................. 9906140

(51) Int. Cl.[7] .............................. C12Q 1/04; C12Q 1/00; G01N 33/53

(52) U.S. Cl. ............................ 435/34; 435/4; 435/968; 435/975; 435/805; 435/810

(58) Field of Search .............................. 435/34, 4, 975, 435/968, 805, 810

(56) References Cited

U.S. PATENT DOCUMENTS 4,355,102 A    10/1982  Quash ......................... 435/34
6,472,167 B1 * 10/2002  Townsend et al.

OTHER PUBLICATIONS

Saito et al, Histochem. Cell Biol., vol. 117(5), May 2002, p 453–458 (Abstract).*
Wiggins et al., "Enzyme Activity of The Vaginal Microflora and its Effect on the Secreted Cervical Mucus Barrier," British Journal of Nutrition (ISSN 0007–1145) vol. 88, Supplement 1, pp. S119–120, 2002.
Masfari et al., "Quantitative studies of vaginal bacteria", Department of Medical Microbiology, University of Sheffield Medical School, and the Department of Genitourinary Medicine, Accepted for publication Dec. 16, 1985, pp. 256–263.
Millar et al., "Application of 16S rRNA Gene PCR To Study Bowel Flora of Preterm Infants with and without Necrotizing Enterocolitis", Journal of Clinical Microbiology, Received Apr. 18, 1996, Returned for modification Jun. 13, 1996, Accepted Jul. 15, 1996, Oct. 1996, vol. 34, No. 10, pp. 2506–2510.
Characterization of Cervical Mucus in Pregnancy and the Mucinase Activity of Vaginal Bacteria, Published Sep. 7/8, 1998. Abstract for Poster Presentation–Tommy's Campaign, London.
Corfield et al., "Increased Salidase Activity in Women with Bacterial Vaginosis," Prenatal and Neonatal Medicine, vol. 3, Suppl. 2, p. 20, ISSN: 1359–8635.
Puapermpoonsiri S. et al., "Vaginal Microflora Associated with Bacterial Vaginosis in Japanese and Thai Pregnant Women," Clinical Infect. Dis. vol. 23, pp. 748–752, (1996).
Briselden A.M., et al., "Sialidases (Neuraminidases) in Bacterial Vaginosis and Bacterial Vaginosis–Associated Microflora," J. Clin. Microbol. vol. 30 (3), pp. 663–666, (1992).
Fujii I. et al., "X–neu5Ac: A Novel Substrate for Chromogenic Assay of Neuraminidase Activity in Bacterial Expression Systems," Bioorg. Med. Chem. vol. 1 (2) pp. 147–149, (1993).
Corfield et al., "Mucin Degradation in the Human Colon: Production of Sialidase Sialate O–Acetylesterase, N–Acetylneuraminate Lyase, Arylesterase, and Glycosulfatase Activities by Strains of Fecal Bacteria," Infect. Immunol., 60: 3971–3978 (1992).
Corfield et al., "The Roles of Enteric Bacterial Sialidase, Sialate O–Acetyl Eterase and Glycosulfatase in the Degradation of Human Colonic Mucin," Clycoconjugate Jour. 10: 72–81 (1993).
Corfield et al., "Colonic Mucins in Ulcerative Colitis: Evidence for Loss of Sulfation," Clycoconjugate Jour. 13: 809–822 (1996).
Ehrenhaft P.M., "Changing Prognosis for Very Low Birth Weight Infants," Obstetrics Gynecol., 74: 528, (1989).
Lamont et al., "The Role of Mycoplasmas, Ureaplasmas and Chlamydiae in the Genital Tract of Women Presenting in Spontaneous Early Preterm Labour," J. Med. Microbiol. 24: 253–257 (1987).
McGregor et al., "Bacterial Vaginosis is Associated with Prematurity and Vaginal Fluid Mucinase and Sialidase: Results of a Controlled Trial of Topical Clindamycin Cream," Am. J. Obstetrics Gynecol., 170: 1048–1059 (1994).
Millar et al., "Enteral Feeding of Premature Infants with *Lactobacilus GG*," Arch Dis Child 69: 483–487 (1993).
Minkoff et al., "Risk Factors for Prematurity and Premature Rupture of Membranes: A Prospective Study of the Vaginal Flora in Pregnancy," Am J. Obstetrics Gynecol., 150: 965–972 (1984).
Nugent et al., "Reliability of Diagnosing Bacterial Vaginosis is Improved by a Standardized Method of Gram Stain Interpretation," J. Clin. Microbiol, 29: 297–301 (1991).

(List continued on next page.)

Primary Examiner—Louise N. Leary
(74) Attorney, Agent, or Firm—Beyer Weaver & Thomas, LLP

(57) ABSTRACT

A method for the detection of a disease comprising the steps of: (i) obtaining a biological sample from a human subject; (ii) applying the biological sample to a sialidase substrate which has been immobilized on a solid support medium; and (iii) detecting a change in the immobilized sialidase substrate is provided. The substrate is preferably 5-bromo-4-chloro-3-indoyl α-D-N-acetyl neuraminic acid or a salt thereof.

7 Claims, No Drawings

OTHER PUBLICATIONS

Spiegel et al., "Diagnosis of Bacterial Vaginosis by Direct Gram Stain of Vaginal Fluid," J. Clin. Microbiol., 18: 170–177 (1983).

Thornton et al., "Methods of Separation and Deglycosylation of Mucin Subunits," Analy. Biochem., 227: 162–167 (1994).

Von Itzstein et al., "Rational Design of Potent Sialidase-Based Inhibitors of Influenza Virus Replication," Nature 363: 418–423 (1993).

Chemical Abstracts, vol. 120, No. 15: Apr. 11, 1994, US; Abstract No. 192216r, p. 1103; column 2; XP002901153 abstract & JP OS 339283A (Tanpaku Kaogaku Kenkyush KK) Dec. 21 (1993).

McGregor et al., "Bacterial Vaginosis is Associated with Prematurity and Vaginal Fluid Mucinase and Sialidase: Results of a Controlled Trial of Topical Clindamycin Cream," Am. J. Obstetrics Gynecol., 170:1048–1060 (1994).

Moncla B.J. and Braham P., "Detection of Sialidase (Neuraminidase) Activity in Actinomyces Species by Using 2'–(4–Methylumbelliferyl)–a–D–N–Acetylneuraminic Acid in a Filter Paper Spot Test," J. Clin. Microbiol. vol. 27, pp. 182–184, (1989).

Wiggins et al., "Enzyme Activity of The Vaginal Microflora and its Effect on the Secreted Cervical Mucus Barrier," Published Sep. 7/8, 1998. Abstract for Poster Presentation – Tommy's Campaign, London.

Wiggins et al., "Purification of Cervical Mucus in Pregnancy and the Mucinase Activity of Vaginal Bacteria," Published Apr. 2/3, 1998, pp. S54–S55, Abstract for Poster Presentation–British Maternal and Fetal Medicine Society, Manchester.

Howe et al., "Mucinase and Sialidase Activity of the Vaginal Microflora: Implications for the Pathogenesis of Preterm Labour," International Journal of STD & AIDS, 1999; 10: 442–447.

Stark et al., "Mucinase Activity," Methods in Molecular Biology, vol. 125: pp. 385–392, (1998).

Wiggins, et al., "Use of 5–Bromo–4–Chloro–3–Indolyl–a–D–N–Acetylneuraminic Acid in a Novel Spot Test to Identify Sialidase Activity in Vaginal Swabs from Women with Bacterial Vaginosis," J. of Clin. Microbiol., vol. 38, No. 8, pp. 3096–3097 (2000).

Adinolfi, et al., Detection of Trisomy 18 and Y–Derived Sequences in Fetal Nucleated Cells Obtained by Transcervical Flushing, The Lancet, vol. 342: pp. 403–404, (1993).

Briselden, et al. "Sialidases (Neuraminidases) in Bacterial Vaginosis and Bacterial Vaginosis–Associated Microflora," J. Clin. Microbiol., 30: 663–666, (1992).

Colina et al., "Evidence for Degradation of Gastrointestinal Mucin by *Candida Ablicans* Secretory Aspartyl Proteinase," Infect. Immun., 64: 4514–4519, (1996).

Corfield et al., "Detection of Carbohydrate Sulphatase in Human Faecal Extracts," Biochem. Soc. Trans., 15: 1089, (1987).

Corfield et al., "Degradation by Bacterial Enzymes of Colonic Mucus from Normal Subjects and Patients with Inflammatory Bowel Disease: The Role of Sialic Acid Metabolims and the Detection of a Novel O–acetylsialic Acide Esterase," Clin. Sci., 74: 71–78 (1988).

Wiggins et al., "Use of 5–Bromo–4–Chloro3–Indolyl–a–D–N–Acetylneuraminic Acid in a Novel Spot Test to Identify Sialidase Activity in Vaginal Swabs fom Women with Bacterial Vaginosis," J. Clin. Microbiol., 38: 3096–3097 (2000).

Holmes et al., "A prospective Study of Maternal Serum Insulin–Like Growth Factor–I in Pregnancies with Appropriately Grown or Growth Restricted Fetuses," British Journal of Obstetrics and Gynaecology, 105: 1273–1278, (1998).

Wiggins, et al., "Mucinases and Sialidases: Their Role in the Hogenesis of Sexually Transmitted Infections in Female Genital Tract," Sex. Transm. Inf., 77: 402–408 (2001).

Sheehan et al., "Physical and Biochemical Changes in Cervical Mucins Through the Ovulatory Cycle," Gltconj. J. 12:494 (1995).

* cited by examiner

DIAGNOSTIC TEST

This invention relates to a method for the detection of a disease, a device for use in such a method and a kit comprising such a device.

Bacterial vaginosis (BV) is a condition in which the most numerous micro-inhabitants of the vagina (Lactobacilli) are overwhelmed by other micro-organisms such as *Gardnerella vaginalis*. BV is associated with preterm labour (PTL). The mechanism behind this association is thought to be due to BV-related flora gaining access to the uterus and causing the release of inflammatory mediators that initiate labour.

It has previously been thought that in BV, the bacterial infection itself gives rise to PTL. Antibiotics are commonly used to treat BV, for example to prevent PTL, but such tratment is rarely successful. Moreover antibiotics can remove non-pathogenic bacteria, including beneficial strains such as Lactobacilli.

At present, the presence of BV is detected on the basis of a clinical examination and Gram staining for the bacteria characteristic of the disease. It takes a few days in order to get a result using Gram staining so the patient cannot be told the result at the time of visiting the clinic.

During pregnancy, there is no membranous barrier between the vagina and the uterus to prevent an ascending bacterial infection. However, the cervical mucus plug is thought to act as a physical barrier to in-utero infection.

The mucus plug is built on an infrastructure of carbohydrate-rich glycoproteins called mucins. Mucins are composed of oligosaccharide side chains joined to a central protein core. Sialic acid residues are present at the terminal ends of the carbohydrate side-chains.

High levels of bacterial sialidase activity are found in the vaginal secretions of women with BV as opposed to those without BV(MacGregor et al (1994) Am. J. Obstet. Gynaecol. 170 1048–1060; Briselden et al (1992) J. Clin. Microbiol. 30 663–666).

Bacterial sialidases are enzymes which cleave sialic acid residues of glycolipids and glycoproteins. To date, sialidase activity has been assayed by colorimetric, fluorimetric and radioactive techniques using a variety of natural and synthetic sialoglycoconjugate substrates. Substrates which have previously been used in assays for sialidase activity include: bovine submandibular gland mucin and human α-1 acid glycoprotein (Howe et al (1999) in press); 2'-(4-methylumbelliferyl)-α-D-N-acetylneuraminic acid (Paupermpoonsiri et al (1996) Clin. Inf. Dis. Vol. 23 748–752; Brieselden et al (1992) supra); 4-nitrophenyl-α-sialic acid and 2-(3-methoxyphenyl)-N-acetyl-D-neuraminic acid (MacGregor et al (1994) supra). The sensitivity of many of the known sialidase substrates is low.

The sialidase substrates described to date are used in a variety of assays. For example, colorimetric or fluorimetric assays may be used with synthetic substrates, which detect the non-sialic moiety of the substrate (for example 4-methyl umbelliferone or 4-nitrophenol). Alternatively, the amount of sialic acid released from a sialoglycoconjugate substrate can be deteced by HPLC or a colorimetric assay. Also, radioactive assays are sometimes used which involve the introduction of a radiolabel into the sialoconjugate substrate and detection of the released sialic acid by liquid scintillation counting.

The present inventors have discovered that the link between PTL and BV is due to bacterial sialidase activity rather than bacterial infection itself. It is believed that sialidase activity is involved in the degradation of the mucus plug, which results in increased bacterial access into the upper reproductive tract.

The carboxyl groups of the sialic acids at the ends of the carbohydrate side-chains of the mucin molecules confer a negative ionic charge causing rigidity of the sugar side chains. Cleavage of sialic acid destroys the mutual repulsive charge between the mucin molecules causing a loss of viscosity of the mucus plug. Bacterial access into the upper reproductive tract is increased as a result of this action for two reasons. Firstly, mucin and therefore mucus matrix organisation is lost after degradation and the mechanical and bacteriostatic properties of the mucus matrix are rendered less effective as barrier mechanisms. Secondly, disintegration of the mucus layer facilitates bacterial adherence to the underlying epithelium which alters immunological recognition responses and reduces the likelihood that bacteria will be washed out by the movement of the vaginal fluid.

It follows from this discovery that sialidase inhibitors should be useful to treat and prevent conditions such as bacterial vaginosis, and will be useful in therapies to prevent PTL. It also follows that assays for sialidase activity will be useful to detect diseases such as BV.

The present inventors have also developed a diagnostic test for diseases such as BV which detects the presence of sialidase activity. A result in this test has been found to correlate significantly with the incidence of BV using a conventional Gram-stain diagnosis. The test method involves taking a sample from a patient and contacting the sample with a sialidase substrate. After incubation, detectable change such as a colour change, is observed if sialidase activity is detected. In a preferred embodiment, the test is a spot test, that is to say that the sample is applied to the sialidase substrate which is itself supported by a suitable solid medium, such as a filter paper.

The test makes use of substrates which have been found to have a very high sensitivity in the detection of BV, indicating possibly an optimum environment for the binding of sialidases from BV flora. The preferred substrate used in the present test is a salt of 5-bromo-4-chloro-3-indoyl α-D-N-acetyl neuraminic acid, in particular the cyclohexyl amine (X-α-NANA), which is available for Rose Scientific Ltd., Edmonton, Canada.

The test method of the present invention for detecting sialidase activity is highly sensitive, inexpensive to run and quick and simple to use. The test is especially useful to test for sialidase activity as an indicator of BV and therefore a predictor of the likelihood of preterm birth. The assay can be carried out in the same room as the patient or in a clinic or GP surgery, since the method of the invention does not require the use of items of expensive equipment or materials other than those which would normally be available. For example, in contrast to conventional methods, there is no need for a Gram staining kit or a light microscope. Moreover, the method of the invention is less labour intensive than a Gram stain.

Also, the sialidase spot test has an advantage over the calorimetric, fluorimetric or radioactivetests which are currently used to detect BV in that, since sialidase activity is not always present in BV or in all BV flora, its presence may be an indicator that the condition is more detrimental to the host in some cases than in others.

According to a first aspect of the invention there is provided a method for the detection of a disease comprising the following steps:

(i) obtaining a biological sample from a human subject;
(ii) applying the biological sample to a sialidase substrate which has been immobilised on a solid support medium; and
(iii) detecting a change in the immobilised sialidase substrate.

According to a second aspect there is provided a device for use in the detection of a disease, which device comprises a sialidase-specific substrate immobilised on a solid medium.

The device may be used in a method according to the first aspect of the invention, which comprises the following steps:

i) obtaining a biological sample from a human subject;
ii) applying the biological sample to the device; and
iii) detecting the presence or absence of a colour change in the immobilised sialidase substrate According to a third aspect of the invention there is provided a kit for the diagnosis of a disease which comprises a device according to the second aspect of the invention.

The kit of this third aspect of the invention may also comprise an incubation medium, for example a Tris/HCl buffer and/or a sample-obtaining means.

Preferably the device of the second aspect of the invention and the kit of the third aspect of the invention is used to diagnose a genito-uninary tract infection. More preferably the disease is bacterial vaginosis.

The sialidase sustrate is a substrate which is recognised specifically by a sialidase enzyme. For example, the substrate may be cleaved by the sialidase enzyme. Preferably the substrate is a glycoside of sialic acid. More preferably the substrate is 5-bromo-4-chloro-3-indoyl α-D-N-acetyl neuraminic acid or a salt thereof, for example the cyclohexyl amine salt thereof.

The solid medium may be, for example, filter paper.

Preferably the mammalian subject is a pregnant woman or a woman who is contemplating pregnancy.

According to a fourth aspect of the present invention, there is provided a method for the detection of sialidase activity in a sample, which method comprises the following steps:

(a) contacting said sample with a test reagent comprising 5-bromo-4-chloro-3-indoyl α-D-N-acetyl neuraminic acid or a salt thereof; and
(b) detecting a change in the test reagent.

The test reagent may comprise, for example, a solid, liquid or gel phase medium on or in which the 5-bromo-4-chloro-3-indoyl α-D-N-acetyl neuraminic acid or salt thereof is supported, applied, adsorbed or otherwise contained.

The 5-bromo-4-chloro-3-indoyl α-D-N-acetyl neuraminic acid is prefeably in the form of the cyclohexylamine salt. Preferably, the 5-bromo-4-chloro-3-indoyl α-D-N-acetyl neuraminic acid cyclohexyl amine is supported or adsorbed on a solid substrate, for example a filter paper. In this way, the reactive compound may be immobilised on the substrate to facilitate the carrying out of the diagnostic test. Such a diagnostic test where the reactive compound is adsorbed on a solid medium is often referred to as a spot-test, since the diagnostic test itself is carried out by "spotting" the sample (or an extract of the sample) onto the solid medium in the area where the reactive compound has been adsorbed.

The sample may be obtained directly from a mammalian subject, typically a human subject, for example as a swab, or a washing using a suitable buffer. After the sample has been taken, it may be applied to or contacted directly with the test reagent. Alternatively, for example where the sample is a swab, the contents of the sample may be extracted in a liquid medium, for example a buffer such as tris buffer and then applied to the test reagent. This may make application of the test method more convenient.

The test method is particularly suited for the detection of BV, and so, in a preferred embodiment, the sample is taken as a vaginal swab or sample from a female human patient.

After the sample has been contacted with the test reagent, any change in the test reagent is observed. In the case where the test reagent comprises 5-bromo-4-chloro-3-indoyl α-D-N-acetyl neuraminic acid cyclohexyl amine, the change is a colour change, from colourless to blue. This change may be observed visually, or may be carried out using suitable equipment, such as a stick test calorimeter or a spectrophotometer, which could be used to quantify the result. Where a colour change is to be observed, it is preferred that the background part of the substrate is not of a colour which would obscure or mask the colour change in the reactive compound. It is also preferred that the unreacted test reagent is of a colour which does not show up on the background part of the substrate. Preferably the unreacted test reagent is colourless.

According to a fifth aspect there is provided a kit for use in the fourth aspect of the present invention, which comprises a test reagent comprising 5-bromo-4-chloro-3-indoyl α-D-N-acetyl neuraminic acid or a salt thereof.

In this embodiment of the invention, the test reagent is preferably a device in the form of a solid medium on which the 5-bromo-4-chloro-3-indoyl α-D-N-acetyl neuraminic acid or salt thereof is supported or adsorbed. The preferred test reagent is a filter paper soaked in 5-bromo-4-chloro-3-indoyl α-D-N-acetyl neuraminic acid cyclohexyl amine solution. Preferably the filter paper is soaked in a solution of 5-bromo-4-chloro-3-indoyl α-D-N-acetyl neuraminic acid cyclohexyl amine at approximately 1 mg/ml. The filter paper can then be used directly or dried and stored for future use. Hence the kit can either comprise 5-bromo-4 chloro-3-indoyl α-D-N-acetyl neuraminic acid cyclohexyl amine (for example in solution) and a solid medium (for example filter paper) such that the user can apply the substrate to the solid medium, or the kit can comprise a solid medium to which 5-bromo-4-chloro-3-indoyl α-D-N-acetyl neuraminic acid cyclohexyl amine solution has been previously applied and dried.

The kit of this aspect of the invention may also comprise an incubation medium, for example a Tris/HCl buffer and/or a sample-obtaining means, and may be packaged together in a suitable container with appropriate instructions for use.

The test reagent used in the present invention may be prepared by a process in which the reactive compound is brought into contact with a suitable solid, liquid or gel phase medium so that the reactive compound is contained in or supported or adsorbed on the medium. For example, where the test reagent is a solid device, the reactive compound may be prepared in a suitable solution which is then applied to the solid medium.

The test reagent employed in the fourth and fifth aspects of the present invention is itself an aspect of the present invention. A preferred form of the reagent is a solid device in which the test reagent is applied to a surface of a solid substrate to form a local patch which is where the diagnostic test is carried out.

The method of the fourth aspect of the invention, the kit of the fifth aspect of the invention and the device of the sixth aspect of the invention may be used to detect a disease which is characterised by abnormal (for example increased) activity of bacterial sialidases. For example, the disease may be a genito-uninary tract infection. Preferably the method of the fourth aspect of the invention, the device of the fifth aspect of the invention and the kit of the sixth aspect of the invention is used to diagnose bacterial vaginosis.

Preferably the mammalian subject is a pregnant woman or a woman who is contemplating pregnancy.

According to a seventh aspect of the invention there is provided a method for diagnosing PTL in a human subject which method comprises the step of assaying bacterial sialidase activity in the patient or in a sample taken from the patient.

According to a eigth aspect of the invention there is provided a method for treating BV or preventing PTL which method comprises the step of administering a sialidase inhibitor to the patient.

According to a ninth aspect of the invention there is provided the use of a sialidase inhibitor in the manufacture of a therapeutic or prophylactic composition for the treatment of BV or for the prevention of PTL.

For a better understanding of the present invention, and to show how the same may be put into effect, reference will now be made, by way of example only, to the following example.

EXAMPLE

A parallel Gram-stain and Sialidase Spot-test Assay for the Diagnosis of BV 100 women attending the Milne Genito-Urinary Clinic, Bristol Royal Infirmary, were tested for sialidase activity in addition to the routine Gram stain for the detection of BV. A separate swab was taken at the time of examination and placed immediately into a buffer composed of 2 mls 25 mM Tris/HCl/Tween 20 (pH 7.0). The swabs were placed in cold store at 4° C. until the end of clinic.

The sialic acid substrate 5-Bromo-4-chloro-3-indolyl-$\alpha$-D-N-acetylneuraminic acid cyclohexylamine salt was weighed out to a concentration of 1 mg/ml in a buffer of 25 mM CaCl, 150M Na acetate and 1M NaCl (pH 5.5). This was mixed well and then pipetted onto a 10 cm diameter piece of filter paper until the filter paper was well damped. The swabs were removed from the Tris buffer and rubbed onto the filter paper inoculated with substrate. The filter paper was placed in a Petri dish, the lid closed and the dish incubated for 1 hour at 37° C. A blue spot would appear indicating sialidase activity was present. If there was no sialidase activity, the paper remained colourless even after a period of 2 hours prior to the filter paper drying out.

Gram stain diagnosis of BV was assessed by Spiegel's criteria (1980). Grade 2 BV as defined by Hay et al (1992) is a problematic category whose relationship to both BV and "normal" vaginal flora needs further elucidation. This category does not fulfil the definition of BV and it is unclear whether Grade 2 BV is an indication that colonization with BV microorganisms undergoes a stepwise progression. In this study, therefore, Grades 1 and 2 were pooled for the purposes of the statistical analysis, although initial assessment of the Gram stains divided them into Grade 1 (predominantly *Lactobacillus morphotypes*), Grade 2 (mixed Lactobacillus and organisms associated with BV) and Grade 3 (few or no Lactobacilli, predominantly BV organisms with the presence of clue cells). Observers were blinded to the results of the spot test and spot test observers were blinded to the results of the Gram-stain.

Results

Gram stain results for BV were correlated with the results of the spot test. The results of Grade 1 and Grade 2 were pooled for the statistical analysis, as Grade 2 is not regarded as a definitive diagnosis of BV and the numbers in this study were relatively small.

The patient's ages ranges were 16 years to 52 years with the mean age being 28.3 years, the median 26 years and the mode 25 years.

A positive spot test for sialidase activity was significantly correlated with the incidence of BV Grade 3 on Gram stain diagnosis at the $p<.000001$ level. The sensitivity of the spot test in the detection of BV was therefore 93.5 and the specificity 96.3. The positive predictive value was 95.6 and the negative predictive value 94.5. Amsells (1990) criteria was significantly associated with the results of the spot test at the $p=.04$ level, with the sensitivity being 93.7, specificity 70.5, the positive predictive value 57.6 and the negative value 96.2.

What is claimed is:

1. A method for the detection of a disease comprising the following steps:
   (i) obtaining a biological sample from a human subject;
   (ii) applying the biological sample to a sialidase substrate 5-bromo-4-chloro-3-indoyl $\alpha$-D-N-acetyl neuraminic acid or a salt thereof, which has been immobilised on a solid support medium; and
   (iii) detecting a change in the immobilised sialidase substrate.

2. A method according to claim 1, wherein the disease is bacterial vaginosis.

3. A device for use in a method for detecting a disease according to claim 1, said device comprises a sialidase-specific substrate immobilised on a solid medium.

4. A kit for the diagnosis of a disease which comprises the device according to claim 3.

5. A method for the detection of sialidase activity in a sample, which method comprises the following steps:
   (a) contacting said sample with a test reagent comprising 5-bromo-4-chloro-3-indoyl $\alpha$-D-N-acetyl neuraminic acid or a salt thereof; and
   (b) detecting a change in the test reagent.

6. A method according to claim 5, wherein the 5-bromo-4-chloro-3-indoyl $\alpha$-D-N-acetyl neuraminic acid is adsorbed on a solid medium.

7. A method according to claim 5, wherein the method is used to detect bacterial vaginosis.

* * * * *